United States Patent [19]

Saldivar, Jr. et al.

[11] Patent Number: 5,501,982

[45] Date of Patent: Mar. 26, 1996

[54] METHOD OF USING A DISPOSABLE REAGENT PACK

[75] Inventors: Louis Saldivar, Jr., Kenosha, Wis.; Sangvorn Rutnarak, Long Grove, Ill.

[73] Assignee: Abbott Laboratories, Abbott Park, Ill.

[21] Appl. No.: 459,377

[22] Filed: Jun. 2, 1995

Related U.S. Application Data

[60] Continuation of Ser. No. 298,446, Aug. 29, 1994, abandoned, which is a division of Ser. No. 169,886, Dec. 20, 1993, abandoned.

[51] Int. Cl.$^6$ ........................................... G01N 1/00
[52] U.S. Cl. ........................... 436/150; 422/63; 422/67; 422/73; 422/100; 422/102; 436/43; 436/174; 436/179
[58] Field of Search ........................ 422/99–102, 63, 422/58, 67, 73; 435/8.9; 436/174, 43, 179, 180; 220/502, 505, 506, 555

[56] References Cited

U.S. PATENT DOCUMENTS

| | | | |
|---|---|---|---|
| 1,262,081 | 4/1918 | Mojonnier . | |
| 3,107,204 | 10/1963 | Brown et al. | 195/103.5 |
| 3,649,464 | 3/1972 | Freeman et al. | 195/140 |
| 3,774,455 | 11/1973 | Seidler et al. | 73/444 |
| 3,933,440 | 1/1976 | Woolley | 23/259 |
| 4,038,149 | 7/1977 | Liner et al. | 195/127 |
| 4,070,249 | 1/1978 | Janine et al. | 195/127 |
| 4,076,592 | 8/1978 | Bradley | 195/103 |
| 4,251,159 | 2/1981 | White | 356/246 |
| 4,265,855 | 5/1981 | Mandle et al. | 422/65 |
| 4,599,315 | 7/1986 | Terasaki et al. | 435/301 |
| 4,727,033 | 2/1988 | Hijikata et al. | 436/69 |
| 4,735,778 | 4/1988 | Maruyama et al. | 422/102 |
| 4,861,554 | 8/1989 | Sakuma | 422/65 |
| 4,933,147 | 6/1990 | Hollar et al. | 422/64 |
| 4,980,293 | 12/1990 | Jeffs | 435/296 |
| 4,986,965 | 1/1991 | Ushikubo | 422/102 |
| 4,990,075 | 2/1991 | Wogoman | 422/58 |
| 5,005,721 | 4/1991 | Jordan | 220/23.4 |
| 5,009,942 | 4/1991 | Benin | 428/36.6 |
| 5,075,082 | 12/1991 | Fechtner | 422/102 |
| 5,094,818 | 3/1992 | Longman et al. | 422/73 |
| 5,128,104 | 7/1992 | Murphy | 422/102 |
| 5,242,660 | 9/1993 | Hsei | 422/102 |
| 5,262,329 | 11/1993 | Carver, Jr. . | |

FOREIGN PATENT DOCUMENTS

| | | |
|---|---|---|
| 0320752 | 6/1989 | European Pat. Off. . |
| 0405729 | 1/1991 | European Pat. Off. . |
| 8402777 | 7/1984 | WIPO . |

OTHER PUBLICATIONS

PCT International Search Report (Form PCT/ISA/210) International Application No. PCT/US94/13559.

*Primary Examiner*—James C. Housel
*Assistant Examiner*—Long V. Le
*Attorney, Agent, or Firm*—Mark C. Bach

[57] ABSTRACT

Methods of using a disposable reagent pack with an analytical instrument to analyze a blood sample are provided. According to one embodiment, a disposable reagent pack comprising a sample well, a lysing solution well, and a red blood cell analytic sample well is used. A blood sample is placed into the sample well and the red blood cell analytic sample well. Fluid is selectively transferred between the sample well and the lysing solution well. Both the lysing solution well and the red blood cell analytic sample well are simultaneously presented to the analytical instrument for analysis.

2 Claims, 4 Drawing Sheets

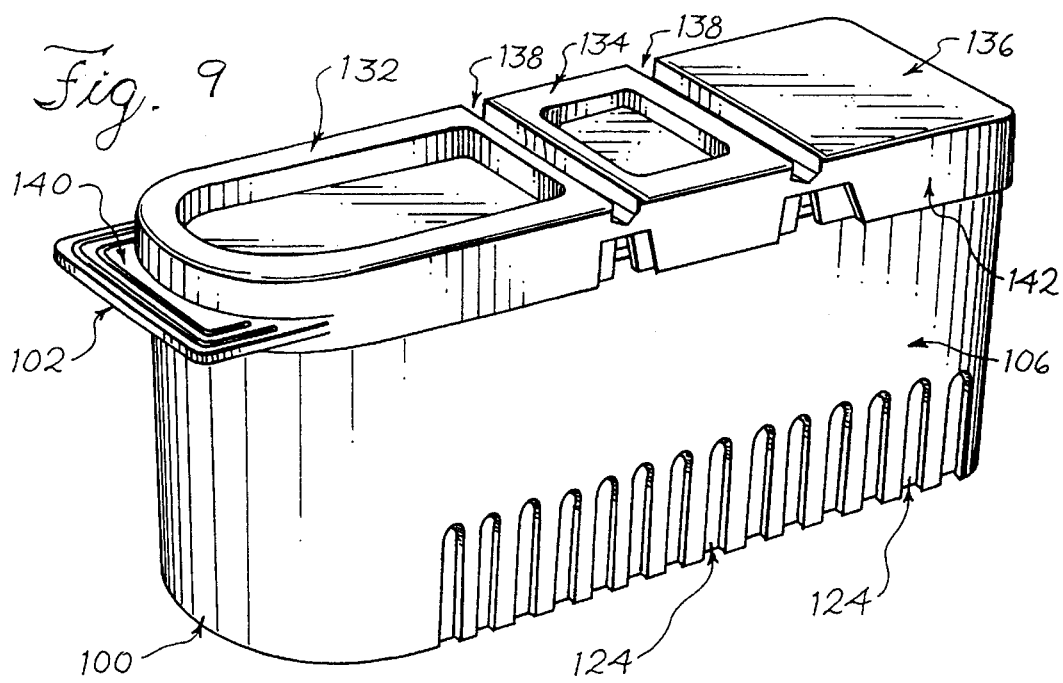
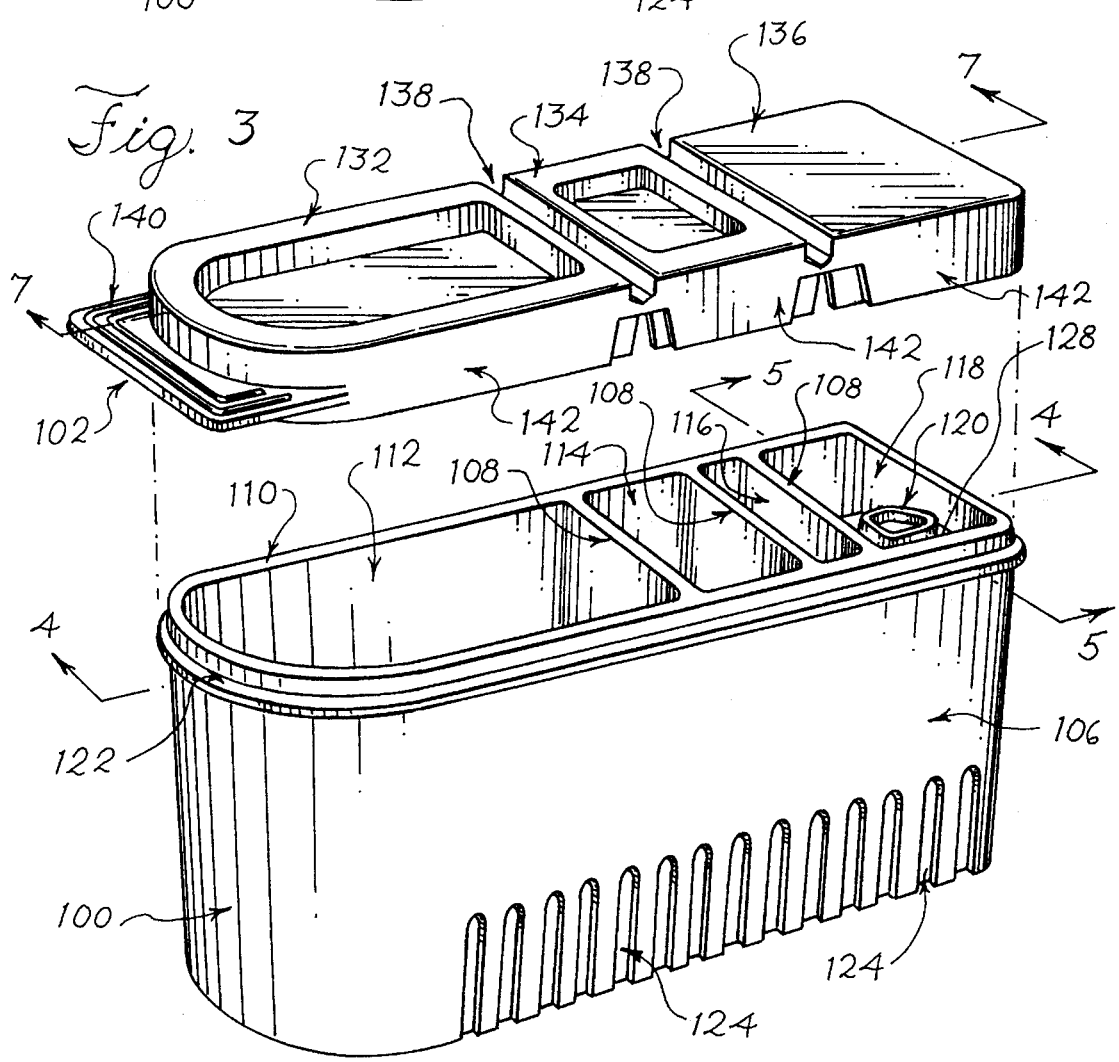

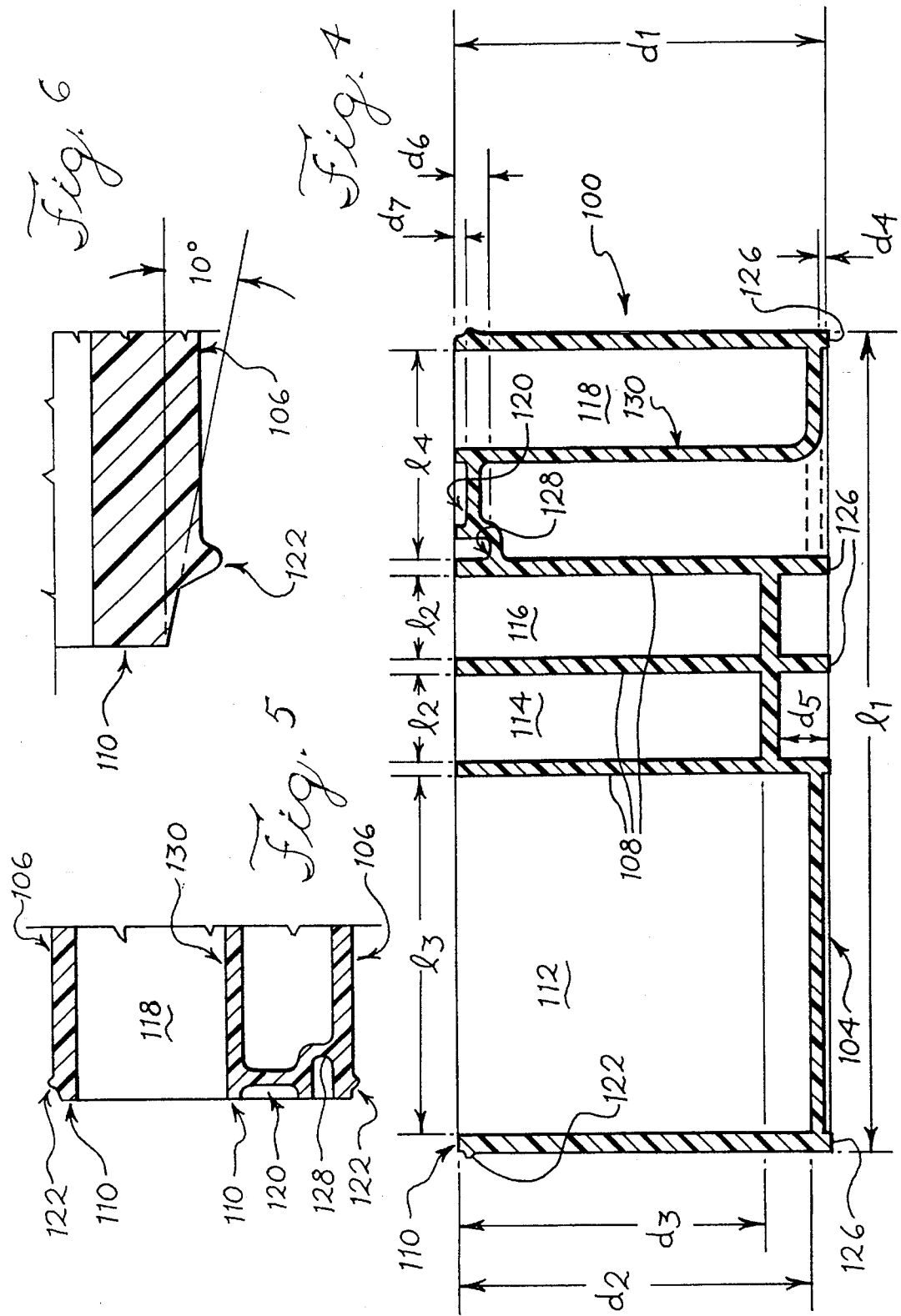

METHOD OF USING A DISPOSABLE REAGENT PACK

REFERENCE TO RELATED APPLICATIONS

This application is a continuation of application Ser. No. 08/298,446, filed Aug. 29, 1994, which is a divisional of U.S. Ser. No. 08/169,886, filed Dec. 20, 1993, all abandoned.

BACKGROUND OF THE INVENTION

The present invention is directed to a method of using a disposable reagent pack usable with analytical instruments and, in particular, to a method of using a reagent pack having an isolation well to control the length of exposure of a first fluid to a second fluid. Embodiments of the present invention control the length of exposure of the first fluid to the second fluid by allowing selective transfer of fluid between the wells containing the respective fluids.

In general, particle analyzers move suspended biological or industrial particles from a sample vessel to a sensor with a liquid system. The sensor detects, counts and identifies the particles in the sample solution. The liquid flow system then moves the sample into a waste container. Many of these analyzers need prepared samples for analysis. The preparation may involve mixing the sample with a reagent. A significant drawback of conventional blood cell analytic systems is their incapacity for simultaneous preparation and presentation to the analyzing equipment of both a red cell analytic sample and a white cell analytic sample. Typically, the collected blood is added to a reagent pack which conventionally is in the form of a single tube or container to which the reagent fluid is added for either a red blood cell count or a white blood cell count. This requires the preparation of two separate analytic samples and the performance of two complete analytical machine cycles. Very often the reagent pack is made of glass which adds handling and disposal problems.

In addition, the current design of most reagent packs requires the direct application of a blood sample to a lysing reagent used in performing a white blood cell analysis. The length of time between exposing the blood sample to the lysing reagent and the performance of white cell differentiation or counting, for example, may vary from one sample to another and from one lab to another. It has been determined that the length of exposure of a blood sample to a lysing reagent of the cationic detergent family, i.e. quaternary ammonium salts, results in cell impedance changes. Therefore, because of this variation in the length of exposure, it is difficult to obtain results which are easily reproducible from one test to another, from one lab to another or even one lab technician to another. U.S. Pat. No. 4,485,175 (Ledis et al.) discloses altering the kinetics of the reaction in an automated instrument to solve this problem, for example, by predilution of the sample or slow addition of the sample to the reagent.

It is desirable to provide a disposable reagent pack wherein the length of exposure time of a first fluid, such as a blood sample, to a second fluid, such as a lysing reagent, is controllable, accurate and reproducible. In addition, it is desirable to provide a disposable reagent pack that is lightweight and durable and which enhances an analytical instrument's efficiency by simultaneously providing both a prepared red blood cell sample and a prepared white blood cell sample for analysis.

SUMMARY OF THE INVENTION

A method of using a disposable reagent pack with an analytical instrument having a probe to analyze a blood sample is provided by the embodiments disclosed herein. A disposable reagent pack is provided comprising a blood sample well and a lysing solution well relatively disposed such that blood sample and lysing solution may be selectively transferred between the blood sample well and the lysing solution well. A cover is placed on the disposable reagent pack. The disposable reagent pack is inverted to selectively transfer blood sample and lysing solution. The cover is removed from the disposable reagent pack. The disposable reagent pack is placed on the analytical instrument. The probe is inserted into the lysing solution well. The probe analyzes the blood sample. The disposable reagent pack is removed from the analytical instrument.

According to another embodiment, a disposable reagent pack is provided comprising a sample well located at a first position, and a reagent well located at a second position with the first position and the second position being predetermined such that fluid may be selectively transferred between the reagent well and the sample well. A lysing solution is placed into the reagent well and blood is placed in the sample well. The disposable reagent pack is moved such that blood in the sample well is selectively transferred with the lysing reagent in the reagent well. A probe is inserted into the reagent well to analyze the blood.

In another embodiment, a disposable reagent pack comprising a blood sample well and a lysing solution well is used. Lysing solution is placed in the lysing solution well and blood sample is placed in the blood sample well. Lysing solution and blood sample are selectively transferred between the blood sample well and the lysing solution well to limit exposure of the blood sample to the lysing solution.

In still a further embodiment, a lysing solution is placed in a disposable reagent pack. A blood sample is placed in the disposable reagent pack such that the blood sample is separated from the lysing solution. A probe is inserted into the disposable reagent pack to analyze the blood sample. Impedance changes detected by the probe are corrected by controlling exposure time of the blood sample to the lysing reagent.

In yet another embodiment, a disposable reagent pack comprising a sample well, a lysing solution well, and a red blood cell analytic sample well is used. Blood sample is placed into the sample well and the red blood cell analytic sample well. Fluid is selectively transferred between the sample well and the lysing solution well. Both the lysing solution well and the red blood cell analytic sample well are presented simultaneously to the analytical instrument for analysis.

BRIEF DESCRIPTION OF THE DRAWINGS

FIG. 3 is a perspective view of a disposable reagent pack and cover according to a second preferred embodiment of the present invention.

FIG. 4 is a cross-sectional view of the reagent pack of FIG. 3 taken along lines 4—4.

FIG. 5 is a cross-sectional view of the reagent pack of FIG. 3 taken along lines 5—5.

FIG. 6 illustrates a cross-sectional view of a lip located around the exterior perimeter of the pack of FIG. 3.

FIG. 9 is a perspective view of the disposable reagent pack of FIG. 3 with cover secured thereto.

DETAILED DESCRIPTION OF PREFERRED EMBODIMENTS

Figure 1:
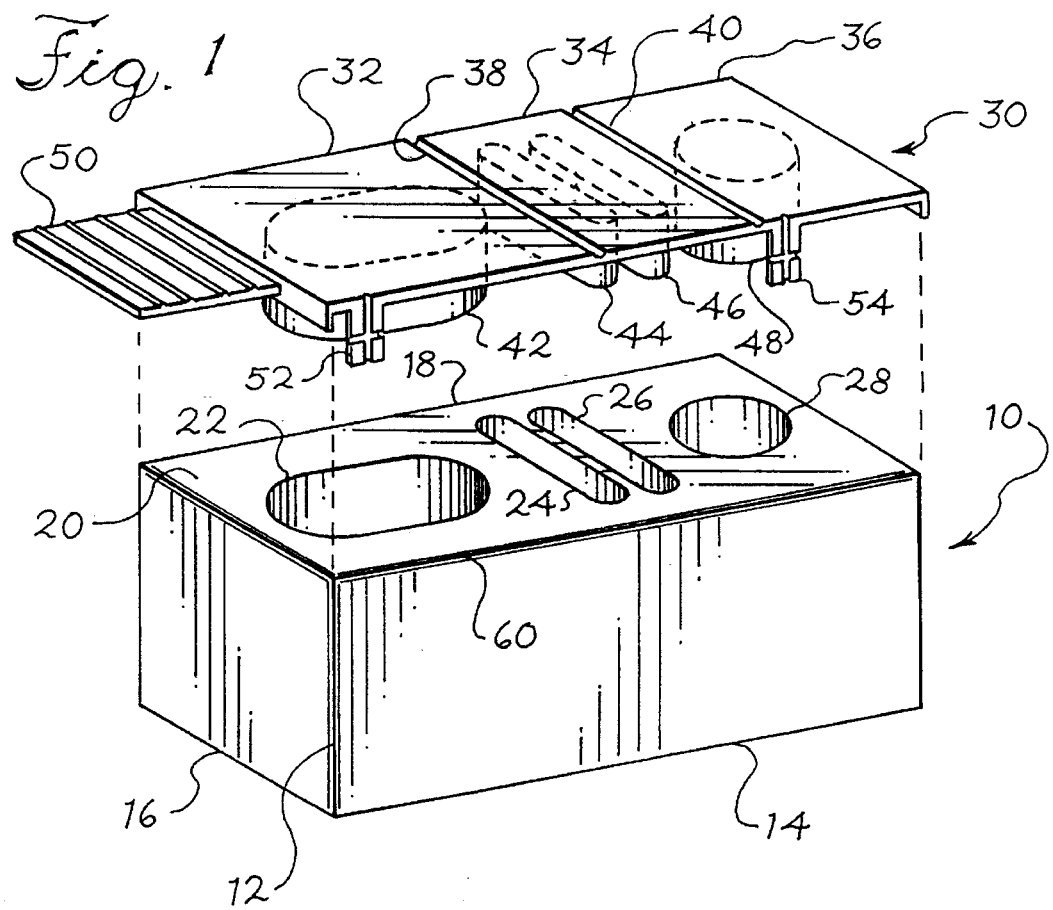
FIG. 1 is a plan view of a disposable reagent pack according to a first preferred embodiment of the present invention.

FIG. 1 is a perspective view of a disposable reagent pack 10 according to a first embodiment of the present invention. In this embodiment, the reagent pack 10 is made of a molded plastic and includes outer side walls 12, 14, 16 and 18 and a top wall 20. The top wall 20 is formed integrally along its length with a first elliptical well 22, second and third elliptical wells 24 and 26 and a fourth circular well 28. Other shapes of these wells are also possible. The major axis of the first well 22 is displaced 90° from the major axis of the second and third wells 24 and 26.

Each of the wells extend downward from the top wall 20 to a point just above the ends of the side walls 12, 14, 16 and 18. In some embodiments, a red blood cell analytic sample may be prepared in well 22 which, in that case, contains a diluent, and a white blood cell analytic sample may be prepared in well 28. If well 28 is to be used to prepare a white blood cell analytical sample, then well 28 contains a suitable amount of an appropriate lysing reagent, such as a solution of a quaternary ammonium salt and the like. Since a typical red blood cell analysis requires a significant volume of sample solution, well 22 is formed as an elliptical well allowing it to hold the needed volume of sample solution. Wells 24 and 26 are each preferably formed as an elliptical well allowing them to hold the needed volume while still remaining within a width defined by the top wall 20, which is determined in part by the diameter of circular well 28. Each of the wells 24 and 26 may act as a reagent reservoir.

The reagent pack 10 is preferably provided with a molded plastic cover 30 which, in one embodiment, is separated into three sections 32, 34 and 36 at hinge areas 38 and 40 formed by appropriate molding, perforating, etching of the plastic and the like. The sections 32, 34 and 36 are provided with integrally formed projection members 42, 44, 46 and 48 which correspond respectively to the size and shape of the wells 22, 24, 26 and 28. The projection members 42, 44, 46 and 48 fit snugly into the top of each of the wells. The cover 30 is also provided at one of its ends with a tab member 50 having a width less than the width of the cover 30. Tab member 50 extends outward beyond the side wall 12 of the reagent pack 10 so that the tab 50 can be grasped by the user when the cover 30 is attached to the pack 10 in order to facilitate cover 30 removal. Four locking tabs 52 and 54 (two of which are not illustrated in FIG. 1) are provided at the sides of sections 32 and 36 and extend downward along the side walls 14 and 18 when the cover 30 is attached to the pack 10. The tabs 52 and 54 engage a portion of the edge 60 formed between the top wall 20 and side walls 14 and 18. A portion of the side walls 14 and 18 along with the tabs 52 and 54 limits lateral movement of the cover 30 on the pack 10 and lends additional support to the connection between the cover 30 and the walls 14 and 18.

Figure 2:
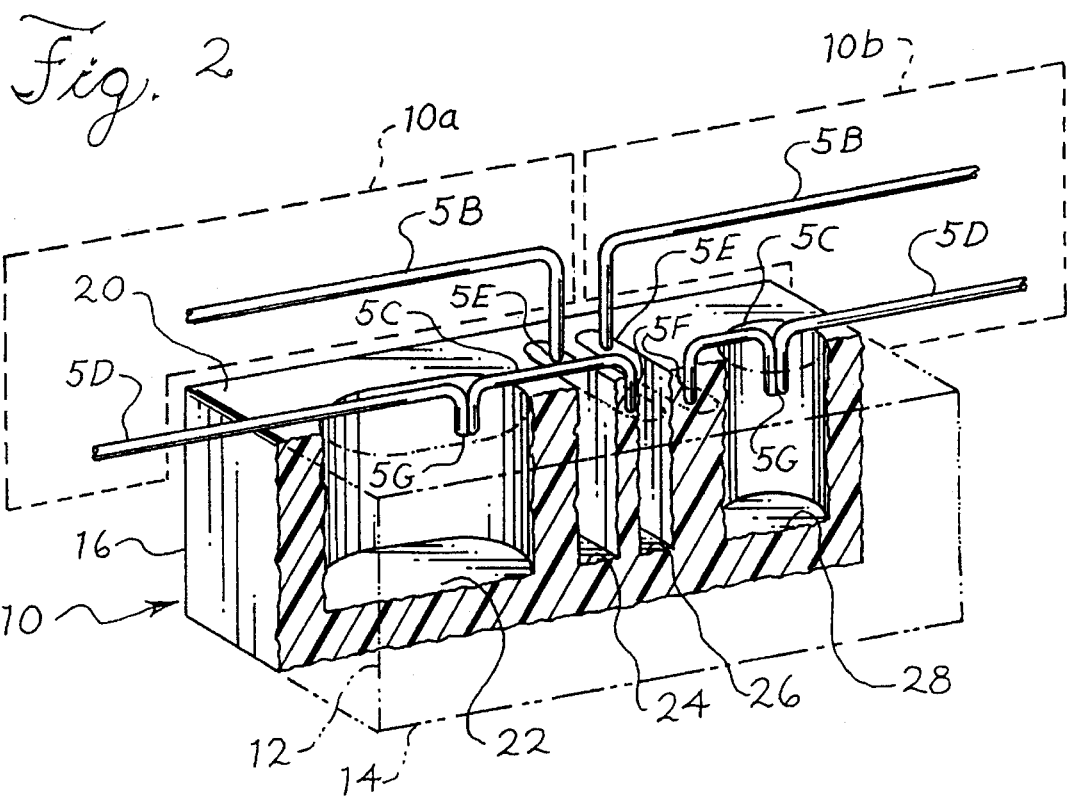
FIG. 2 is a partial schematic of the reagent pack of FIG. 1 in conjunction with an analytical instrument.

FIG. 2 is a partial schematic of the reagent pack 10 of FIG. 1 in conjunction with an analytical instrument. A detailed description of an analytical instrument which may be used with the reagent pack 10 of the present invention can be found in U.S. Pat. No. 5,094,818 and U.S patent application Ser. No. 07/482,007 which, as previously indicated, are incorporated herein by reference. A portion of two substations 10a and 10b of the analytical instrument are illustrated. Sub-station 10a is used to perform the red blood cell analysis and sub-station 10b is used to perform the white blood cell analysis. In operation, an operator removes the cover 30 from the pack 10 which has been prefilled with predetermined amounts of reagent solutions in wells 22, 24, 26 and 28. The necessary amount of blood is introduced into wells 22 and 28. The cover 30 is replaced and the pack 10 is inverted or agitated. The cover 30 is then removed and the pack 10 is loaded onto the analytical instrument for analysis.

The count aperture 5G located in conduit member 5D of sub-station 10a is introduced into the red blood cell analytic sample in well 22, and corresponding waste and fill apertures 5E and 5F in conduit members 5B and 5C are introduced into the corresponding reagent well 24. Thus, the red blood cell sample is ready for analysis. Simultaneously, the count aperture 5G of sub-station 10b is introduced into the white blood cell analytic sample in well 28 and corresponding waste and fill apertures 5E and 5F are introduced into corresponding reagent well 26. Thus, the white blood cell analytic sample is ready for analysis at the same time that the red blood cell sample is presented.

FIG. 3 is a perspective view of a disposable reagent pack 100 and cover 102 constructed according to a second preferred embodiment of the present invention. The reagent pack 100 will be described in detail first, followed by a detailed description of the cover 102. In an exemplary embodiment, the reagent pack 100 is made of a molded polymeric material, such as High Density Polyethylene and the like. The pack 100 includes a base 104, a perimeter wall 106, well separating walls 108 and a top surface 110. Five wells 112, 114, 116, 118 and 120 are illustrated, each well extending downward from a location adjacent the top surface 110 of the pack 100.

Starting from the left end of the pack 100 as viewed in FIG. 3, the first well 112 may be used in red blood cell analysis. Next to the first well 112 is a second well 114 and a third well 116. Well 118, which may be used in white blood cell analysis, is disposed adjacent to the right end of the pack 100 as viewed in FIG. 3. Well separating walls 108 along with the perimeter wall 106, base 104 and top surface 110 define each well except for the isolated well 120 which will be described in detail below. Extending around the exterior surface of the perimeter wall 106 offset from or just below the top surface 110 is a lip 122 which will be described in further detail with reference to FIG. 6.

In an exemplary embodiment, the well 112 defines a volume of about 25 ml, the well 118 defines a volume of about 10 ml, the well 120 defines a volume of about 0.04 ml, and wells 114 and 116 each define a volume of about 5 ml. The isolated well 120 may be used to contain a first fluid, such as a blood sample, and thereby isolate the first fluid from a second fluid, such as reagents, contained in the other wells, and specifically in well 118. In practice, the blood sample deposited in well 120 usually has a volume of about 20 µl. Thus, the well 120 should define a volume somewhat larger than 20 µl in order to provide suitable selective fluid transfer between the wells 118 and 120.

The isolated well 120 is shown in the Figures located in a corner of well 118 to facilitate understanding. However, it may be located anywhere within the perimeter of the well 118 or adjacent thereto. It is to be noted that the entirety of the isolated well 120 need not be contained within the perimeter of the well 118. The isolated well 120 may be located in any position with respect to the well 118 as long as the relative positions of the wells 118 and 120 allow for selective transfer of fluids between the wells 118 and 120 while substantially preventing fluid transfer between either of the wells 118 and 120 and any of the other wells discussed above.

In the illustrated embodiment, the wells 118 and 120 are relatively disposed so as to allow transfer of fluids between the wells 118 and 120 only when the pack 100 is inverted or appropriately agitated. Therefore, the well 120 is suitably configured to insure adequate selective transfer of fluids between the wells 118 and 120. In order to insure that fluid transfer occurs only as intended, other structural variations may be employed. The construction of the cover 102 may be altered. For instance, the portions of the cover 102 adjacent the well 120 may be elongated, enlarged, etc. The integrity of the seal around the well 120 provided by the cover 102 may be increased. Alternatively, the location of the well 120 support or of the well 120 itself may be changed from that shown in the Figures. In such manners, the probability that fluid within the well 120 can be transferred out of the well 120 unintentionally can be reduced.

FIG. 4 is a cross-sectional view of the reagent pack 100 shown in FIG. 3 taken along line 4—4. Referring to both FIGS. 3 and 4, the pack 100 has a length $l_1$ of about 3.70 inches, a depth $d_1$ of about 1.675 inches and a width of about 1.035 inches. The wells 114 and 116 are substantially the same size and have a length $l_2$ of about 0.40 inches and a depth $d_2$ measured from the top surface 110 of about 1.392 inches. Wells 112 and 118 preferably have a depth $d_3$ measured from the top surface 110 of about 1.590 inches. Well 112 has a length $l_3$ of about 1.650 inches and well 118 has a length $l_4$ of about 0.940 inches. The width of wells 112, 114, 116 and 118 is substantially constant at about 0.90 inches except for the left end of the well 112, as viewed in FIG. 4, where the perimeter wall 106 is curved. The wall thickness of the perimeter wall 106 and well separating walls 108 is preferably about 0.060 inches. However, as will be described with reference to FIG. 6, the thickness of the perimeter wall 106 above lip 122 is not uniform. Flutes 124 are formed along the exterior of the perimeter wall 106 on opposite sides of pack 100 to aid the user in grasping the disposable reagent pack 100 and to help reduce the possibility of slippage.

While particular dimensions have been described with reference to this embodiment of the present invention, they are intended only as an example and not a limitation of the present invention. The pack 100 may have other dimensions. Use of these other dimensions may depend upon various factors such as, for example, the type of the analytical instrument used in conjunction with the pack 100, the nature of the tests to be performed in the wells of the pack 100 and the like. In general, the pack 100 is constructed to keep a first fluid in well 118 separate from a second fluid in well 120 until it is desired to mix the two fluids together. When it is desired to mix the two fluids together, the pack 100 allows for selective fluid transfer between the wells 118 and 120. While the pack 100 has been described with reference to its use with analytical instruments, other applications may exist.

The base 104 of the reagent pack 100 will now be described in detail with reference to FIG. 4. In a preferred embodiment, the base surface is raised a distance $d_4$ of about 0.015 inches under wells 112 and 118 and a distance $d_5$ of about 0.220 inches under wells 114 and 116. By raising the base surface under the wells, a rim 126 is formed by a portion of the perimeter wall 106 and the well separating walls 108. The rim 126 helps keep the reagent pack 100 level such as when it is loaded onto an analytical instrument for testing. The deep recesses under wells 114 and 116 are used to elevate fluid levels in the wells 114 and 116 such that the fluid levels in wells 114 and 116 are substantially the same as the fluid levels in wells 112 and 118.

FIG. 5 is an enlarged cross-sectional view of the reagent pack of FIG. 3 taken along line 5—5. A detailed description of the isolated well 120 will now be given with reference to FIGS. 3–5. In the illustrated embodiment, well 120 is located within the perimeter of well 118 and specifically in one corner thereof. Well 120 is joined to the perimeter of well 118 by an "L" shaped ledge 128. The ledge 128 is located a distance $d_6$ of about 0.165 inches from the top surface 110 of the pack 100. Extending upwards from the base of well 118 are three internal walls 130 which support and form a portion of the well 120. The well 120 shares the same top surface 110 as the other wells. The depth $d_7$ of well 120 measured from the top surface 110 of the pack 100 is preferably about 0.050 inches. The importance of ledge 128 will be described with reference to the use of the disposable reagent pack. The ledge 128 allows the well 118 to be sealed while allowing the contents of wells 118 and 120 to be mixed upon inversion of the pack 100.

FIG. 6 illustrates an enlarged cross-sectional view of the lip 122 that extends around the exterior of the perimeter wall 106. In a preferred embodiment, the thickness of the perimeter wall 106 below the lip 122 is substantially constant, measuring about 0.060 inches. The thickness of the wall 106 above the lip 122 is tapered at an angle of about 10 degrees so that the thickness of the wall 106 at the top surface 110 of the pack 100 is about 0.052 inches. Lip 122 extends about 0.09 inches from the outer surface of the perimeter wall 106. The lip 122 has a radius of curvature of about 0.008 inches and is located about 0.063 inches below the top surface 110 of the pack 100.

The cover 102 will now be described with reference to FIGS. 3 and 7–9. In a preferred embodiment, the cover 102 is formed of a flexible, elastomeric material, such as Kraton™ D-0109 available from Shell Chemical Company, other rubber-like materials having a substantially similar durometer and the like. The cover 102 is divided into three main sections 132, 134 and 136. Section 132 covers well 112, section 134 covers wells 114 and 116 and section 136 covers wells 118 and 120. The three sections are connected together at hinge areas 138 formed by suitable means, such as molding, etching, perforation of the material or the like. The cover 102 is also provided at one end with a tab member 140. Tab member 140 extends outwardly beyond the perimeter wall 106 so that it can be grasped by the user when the cover 102 is fastened to the pack 100 in order to facilitate its removal. Locking tabs 142 are provided along the sides of the cover 102 and extend downwardly therefrom. When the cover 102 is placed on the pack 100, inner surfaces 144 of the locking tabs 142 engage the lip 122 formed around the exterior of the perimeter wall 106 of the pack 100.

Figure 7:
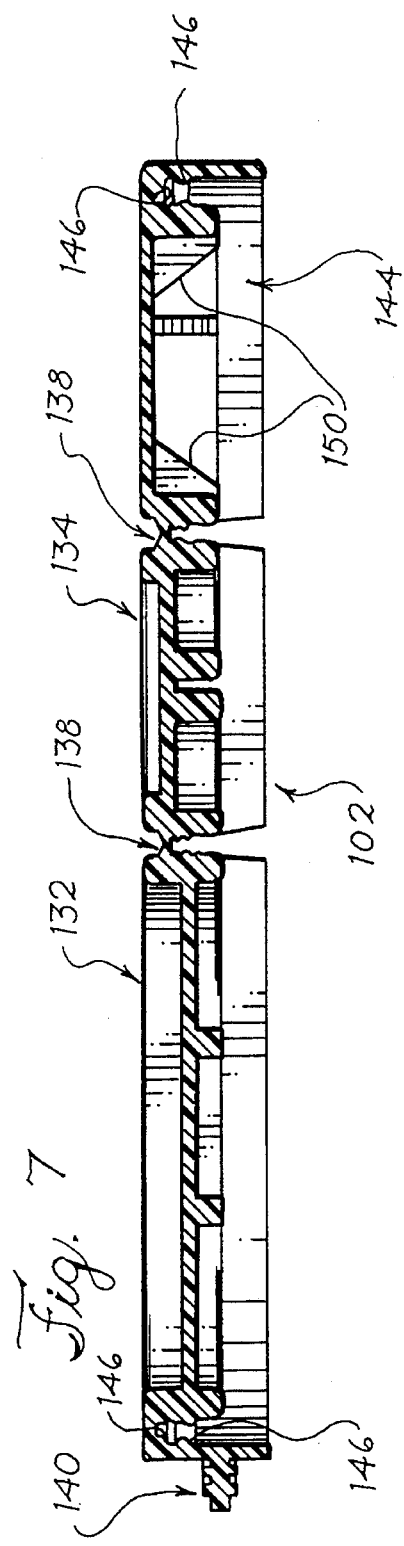
FIG. 7 is a cross-sectional view of the cover of FIG. 3 taken along line 7—7.

FIG. 7 illustrates a cross-sectional view of the cover 102 shown in FIG. 3 taken along lines 7—7. Two ridges 146 are formed and extend around the inner surface 144 of each locking tab 142, i.e. the surface of the locking tab 142 which contacts the exterior surface of the pack 100 when the cover 102 is placed thereon. When the cover 102 is placed on the pack 100, the lip 122 is sandwiched between ridges 146 to secure the cover 102 to the pack 100.

Figure 8:
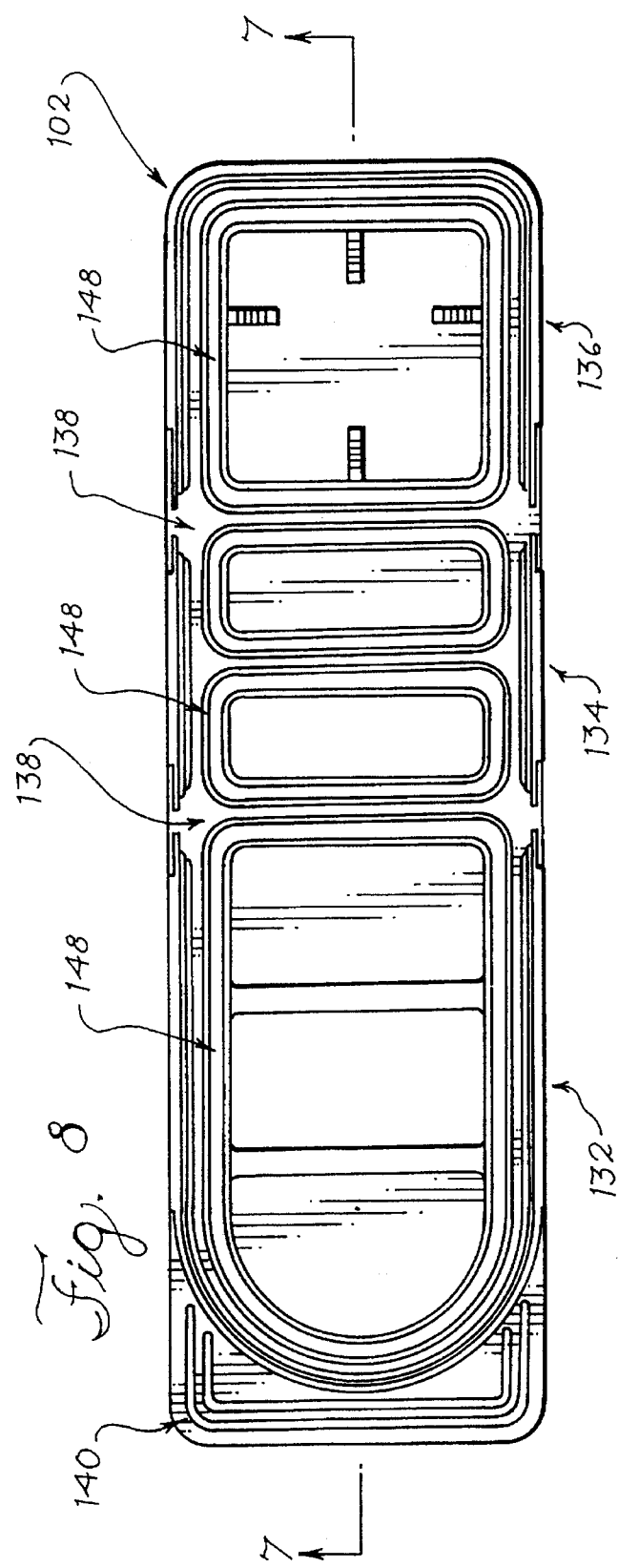
FIG. 8 illustrates the inside of the cover of FIG. 3.

FIG. 8 illustrates the inside of the cover 102. The locking tabs 142 are located around the perimeter of the cover 102.

Spaced a short distance from the locking tabs 142 are well sealing walls 148. The sealing walls 148 are located on the inside of the cover 102 so that they seal the perimeter of wells 112, 114, 116 and 118 and thereby prevent the contents of each well from leaking out of the pack 100 and into the other wells when the pack 100 is inverted.

As described earlier, section 136 covers wells 118 and 120. The sealing wall 148 seals the perimeter of well 118. However, the contents of well 120 are not sealed from the contents of well 118. This is desirable to provide selective transfer of fluid between the wells 118 and 120. Four webs 150 are located within the perimeter defined by the sealing wall 148. A detailed illustration of one web 150 is shown in FIG. 7. The webs 150 increase the rigidity of or stiffen adjacent portions of the cover 102 to insure a tight seal around the wells. When the cover 102 is placed on the pack 100, the sealing wall 148 seals the outer perimeter of well 118. More specifically, because the "L" shaped ledge 128 is located a sufficient distance from the top surface 110 of the pack 100, the sealing wall 148 fits snugly between the inner wall of well 118 and the outer wall of well 120. Upon inversion of the pack 100, selective fluid transfer occurs such that the contents of well 118 are mixable with the contents of well 120.

In an exemplary embodiment, the pack 100 is prepackaged by filling wells 114 and 116 with a reagent solution such as an isotonic solution, such as a lysing reagent and the like. Well 118 is filled with a lysing reagent and diluent solution. The pack 100 may then be covered with a seal, such as a foil member and the like, to prevent the contents of one well from mixing with the contents of another well. Because well 120 is located at the top of well 118, it remains virtually dry. Well 120 is preferably designed to hold substantially more than about 20 μL of fluid to provide adequate room for facilitate mixing of the fluid, such as blood, in well 120 and the fluid, such as an agent, in well 118. It has been discovered that as long as no more than 5 μL of the lysing reagent in well 118 spills into well 120 before the blood sample is added, the test results will not be affected significantly.

To use the pack 100 to perform a blood analysis, for example, the seal is removed and a sample of blood is added to wells 112 and 120. A white blood cell analysis is conducted in well 118 and a red blood cell analysis is conducted in well 112. The cover 102 is placed on the pack 100 as shown in FIG. 9 and the pack 100 is inverted. The inversion of the pack 100 activates the selective fluid transfer and allows the blood sample in well 120 to mix with the lysing reagent and diluent solution in well 118. The pack 100 may be inverted repeatedly to insure proper mixing. After mixing, the cover 102 is removed and the pack 100 may then be loaded onto the platform of an analytical instrument so that testing can proceed.

The analytical instrument described above with reference to the reagent pack 10 of FIG. 1 may also be used with the disposable reagent pack 100 of FIG. 3. For example, when the pack 100 is loaded on the platform of the apparatus, count aperture 5G located on conduit member 5D of sub-station 10a is introduced into the white blood cell analytic sample well 118 and corresponding waste and fill apertures 5E and 5F in conduit members 5B and 5C are introduced into the corresponding reagent well 116. Simultaneously, the count aperture 5G of sub-station 10b is introduced into the red blood cell analytic sample well 112 and corresponding waste and fill apertures 5E and 5F are introduced into corresponding reagent well 114. The white blood cell sample is presented to the instrument for analysis at the same time the red blood cell sample is presented.

After the analytic cycle is completed, the pack 100 is lowered from the point where it contacts the apertures of the system conduits and is removed from the platform. The pack 100 may then be covered and properly disposed.

By providing selective fluid transfer and by isolating the blood sample in well 120 from the lysing solution in well 118 until inversion of the pack 100, as opposed to directly administering the sample to the lysing solution in well 118, the length of exposure of the blood sample to the lysing reagent is controllable and reproducible from test to test and lab to lab. Controlling the length of exposure of a blood sample to a lysing solution reduces changes in the impedance measured by count aperture 5G as a cell is detected. Such impedance changes may negatively affect the test results.

What is claimed is:

1. A method of using a disposable reagent pack with a blood analytical instrument having a red blood cell probe to analyze a red blood cell sample and a white blood cell probe to analyze a white blood cell sample, the method comprising the steps of:

(a) providing a disposable reagent pack comprising a red blood cell sample well and a white blood cell sample well, the white blood sample well being disposed substantially within a lysing solution well such that a blood sample in the white blood cell sample well and a lysing solution in the lysing solution well may be selectively transferred between the white blood cell sample well and the lysing solution well;

(b) placing a cover on the disposable reagent pack;

(c) inverting the disposable reagent pack to selectively transfer and to mix the blood sample in the white blood cell sample well and the lysing solution;

(d) removing the cover from the disposable reagent pack;

(e) placing the disposable reagent pack on the blood analytical instrument;

(f) simultaneously inserting the white blood cell probe into the lysing solution well and the red blood cell probe into the red blood cell sample well;

(g) simultaneously analyzing the red blood cell sample with the red blood cell probe and the white blood cell sample with the white blood cell probe; and (h) removing the disposable reagent pack from the analytical instrument.

2. A method as defined in claim 1 further comprising the step of:

(i) correcting impedance changes detected by the white blood cell probe by controlling exposure time of the white blood cell sample to the lysing solution.

* * * * *